(12) United States Patent
Duarte-Vazquez et al.

(10) Patent No.: US 9,056,134 B2
(45) Date of Patent: Jun. 16, 2015

(54) SINGLE DAILY DOSAGE FORM FOR PREVENTION AND TREATMENT OF METABOLIC SYNDROME

(75) Inventors: Miguel Angel Duarte-Vazquez, Irapuato (MX); Sandra Garcia Padilla, Tula de Allende (MX); Jorge Luis Rosado, Queretaro (MX)

(73) Assignee: NUCITEC S.A. DE C.V., Queretaro (MX)

( * ) Notice: Subject to any disclaimer, the term of this patent is extended or adjusted under 35 U.S.C. 154(b) by 0 days.

(21) Appl. No.: 13/188,265

(22) Filed: Jul. 21, 2011

(65) Prior Publication Data

US 2012/0021049 A1    Jan. 26, 2012

Related U.S. Application Data

(60) Provisional application No. 61/366,395, filed on Jul. 21, 2010.

(51) Int. Cl.
| | | |
|---|---|---|
| *A61K 9/48* | (2006.01) | |
| *A61K 45/06* | (2006.01) | |
| *A61K 31/155* | (2006.01) | |
| *A61K 31/40* | (2006.01) | |
| *A61K 31/403* | (2006.01) | |
| *A61K 31/41* | (2006.01) | |
| *A61K 31/60* | (2006.01) | |

(52) U.S. Cl.
CPC ............... *A61K 45/06* (2013.01); *A61K 9/4808* (2013.01); *A61K 31/155* (2013.01); *A61K 31/40* (2013.01); *A61K 31/403* (2013.01); *A61K 31/41* (2013.01); *A61K 31/60* (2013.01)

(58) Field of Classification Search
None
See application file for complete search history.

(56) References Cited

U.S. PATENT DOCUMENTS

| 2002/0028826 A1* | 3/2002 | Robl et al. ............... 514/290 |
| 2005/0026992 A1* | 2/2005 | Sasmal et al. ............ 514/423 |
| 2007/0015839 A1* | 1/2007 | Folli et al. ............... 514/635 |

* cited by examiner

*Primary Examiner* — Hasan Ahmed
(74) *Attorney, Agent, or Firm* — Sterne, Kessler, Goldstein & Fox P.L.L.C.

(57) ABSTRACT

The present invention is in the fields of medicine, pharmaceuticals, nutraceuticals, endocrinology and cardiology. The invention provides compositions comprising a statin, an inhibitor of the angiotensin converting enzyme, an antiplatelet compound and an anti-hyperglycemic compound for use in the treatment and/or prevention of cardiometabolic risk factors of Metabolic Syndrome and treatment and/or prevention of Metabolic Syndrome. The present invention provides for the use of such compositions in the manufacture of products for treatment and/or prevention of Metabolic Syndrome. The biguanide metformin of the composition could be present in extended release form allowing its use together with the other drugs in a single dosage form at low dose. This combination of drugs in a single daily dosage greatly improves compliance and adherence to treatment which is a critical factor for treating patients with Metabolic Syndrome.

6 Claims, No Drawings

SINGLE DAILY DOSAGE FORM FOR PREVENTION AND TREATMENT OF METABOLIC SYNDROME

BACKGROUND OF THE INVENTION

1. Field of the Invention

The present invention is in the fields of medicine, pharmaceuticals, nutraceuticals, endocrinology and cardiology. The invention provides compositions comprising a statin, an inhibitor of the angiotensin converting enzyme, an antiplatelet compound and an anti-hyperglycemic compound for use in the treatment and/or prevention of cardiometabolic risk factors of Metabolic Syndrome and treatment and/or prevention of Metabolic Syndrome.

2. Related Art

Cardiovascular Disease

Metabolic Syndrome, previously known as Syndrome X, is an intermediate state between normal metabolism and type 2 diabetes mellitus. It is an emerging epidemic which has been defined as a constellation of metabolic risk factors predisposing people to coronary heart disease and chronic kidney disease. The constellation includes abdominal obesity, atherogenic dyslipidemia, hypertension, and proinflammatory and prothombotic states, with or without glucose intolerance. Each of these characteristics is a significant risk factor for development of vascular dysfunction and cardiovascular disease. Important organ systems involved in Metabolic Syndrome include the vasculature, heart, adipose tissue, liver and skeletal muscle.

Although the underlying mechanisms for Metabolic Syndrome have not been entirely elucidated, resistance to the cellular action of insulin is known to be a cardinal feature, as evidenced by the presence of both hyperinsulinemia and insulin resistance in obesity, hypertension, type 2 diabetes mellitus and dyslipidemia.

Abdominal obesity or visceral obesity specifically refers to the accumulation of adipose tissue in the abdominal viscera, and this condition may be visualized through a number of imaging techniques. The anthropometric indices such as the waist circumference, indirectly reflect the abdominal fat, even though they do not discriminate between the subcutaneous or visceral location. The presence of relatively high amounts of adipose tissue generally correspond to a relatively high risk of metabolic changes such as insulin resistance, dyslipidemia and high blood pressure, representing a high risk of diabetes mellitus and cardiovascular disease.

Hypertension is one of the cardinal components of Metabolic Syndrome. Hypertension itself is a major and independent cardiovascular risk factor. Patients with hypertension are more likely to be insulin resistant and in these patients hypertension tends to cluster with other metabolic risk factors.

Dyslipidemia in patients with Metabolic Syndrome is more complex than a simple quantitative derangement of certain lipoprotein particles. Normally, this condition consists of high levels of triglycerides (Tg) and apolipoprotein B (ApoB), small low density lipoprotein cholesterol (LDL-C) particles and low High density lipoprotein cholesterol (HDL-C), that eventually compromise the integrity of the arterial wall. LDL-C is the primary target of therapy in Metabolic Syndrome.

Insulin resistance is characterized as a state in which a typical amount of insulin produced by the pancreas, and resident in the blood stream, fails to interact normally with cells, making it more difficult for glucose to pass from the blood stream into muscle cells, liver cells and adipose tissue cells. Individuals with insulin resistance sometimes have elevated fasting glucose or glucose intolerance. Hyperinsulinemia and insulin resistance are both implicated in the pathogenesis of hypertension, obesity, type 2 diabetes, and atherosclerosis.

Not all risk factors need to be present in an individual to be diagnosed as having Metabolic Syndrome. Normally, Metabolic Syndrome is diagnosed when an individual presents three or more of the following criteria:

a) Abdominal obesity: waist circumference>102 cm in men and >88 cm in woman
 b) Hypertriglyceridemia: ≥150 mg/dL,
 c) Low HDL cholesterol: <40 mg/dL in men and <50 mg/dL in women,
 d) High blood pressure: ≥130/85 mmH, or
 e) High fasting glucose: ≥110 mg/dL.

In addition, prothrombotic and proinflammatory states are related to Metabolic Syndrome. Patients with Metabolic Syndrome often have elevated prothrombotic biomarkers, such as fibrinogen and plasminogen activator inhibitor-1. Likewise, cytokines, such as tumor necrosis factor-α (TNF-α) and interleukin-6 (IL-6), and acute phase reactants, such as C-reactive protein are also elevated. However, currently no definitions have included pro-inflammatory state as component of Metabolic Syndrome.

Treatment of Metabolic Syndrome

The major approaches to manage individuals with Metabolic Syndrome are to reduce the underlying causes and to treat hypertension and other cardiometabolic risk factors and to reduce insulin resistance. Treatment of Metabolic Syndrome includes life style changes along with pharmacologic therapy.

Weight reduction is the first line of intervention in obese individuals with Metabolic Syndrome. Obesity guidelines put emphasis on weight reduction, using behavioral changes to reduce caloric intake and increase physical activity. The first aim of weight loss is to achieve a reduction of about 7% to 10% from baseline total body weight during a period of 6 to 12 months. This requires a caloric intake reduction of 500 to 1000 calories per day. Weight reduction has a synergistic effect on LDL lowering and decreases all of the risk factors of Metabolic Syndrome.

Beyond weight control and reduction of total calories, diet should be low in saturated fats, trans fats, cholesterol, sodium and simple sugars. In addition, there should be an increase in intake of fruits, vegetables and whole grains.

Beyond reducing underlying causes, attention must be given to the metabolic risk factors, such as atherogenic dyslipidemia, hypertension and elevated fasting glucose among others.

Atherogenic dyslipidemia: LDL cholesterol is the primary target of lipid-lowering therapy among individual with Metabolic Syndrome. Statins are a series of substances that inhibit the enzyme 3-hydroxy-3-methylglutaryl-coenzyme A reductase (HMG-CoA) and thus reduce LDL cholesterol. Ezetimibe and bile acid sequestrants are other LDL-lowering agents.

The secondary target of lipid-lowering therapy is non-HDL cholesterol (elevated ApoB) in patients with high triglyceride levels. A tertiary aim in patients with atherogenic dyslipidemia is to raise HDL-C when it is reduced. There are two drug therapy options to achieve secondary and tertiary goals. The first option is to intensify statin therapy, and the second option is to add nicotinic acid or fibrate. However, when fibrate is used in combination with statin, caution should be heeded as there is a high risk for severe myopathy, specially when higher doses of statin are used.

Elevated fasting glucose: In Metabolic Syndrome diagnosis, elevated fasting glucose includes both Impaired Fasting Glucose (IFG) and impaired glucose tolerance (IGT). The American Diabetes Association recommends that metformin should be considered as a drug therapy for individuals with impaired fasting glucose and/or impaired glucose tolerance.

Hypertension: Mild elevation of blood pressure often can be effectively controlled with lifestyle therapies—weight control, increased physical activity, sodium reduction, and increased consumption of fresh fruits and vegetables and low-fat dairy products. If hypertension cannot be adequately controlled by lifestyle therapies, antihypertensive drugs are necessary to prevent long-term adverse effects. Angiotensin converting enzymes (ACE) inhibitors are the first line therapy for hypertension in Metabolic Syndrome.

Prothrombotic and proinflammatory state: There is currently no specific therapy directly acting on prothrombotic or proinflammatory state. Low-dose aspirin may be considered for patients with coronary heart disease, diabetes, or high-risk profile of developing Metabolic Syndrome. C-reactive protein may be used to monitor proinflammatory state in individuals. A high C-reactive protein concentration greater than 3 mg/dL in blood may be used as cut-off indicating higher risk inflammation associated with Metabolic Syndrome. Medications such as statins, nicotinic acid, fibrates, ACE inhibitors, and thiazolidinediones, can also decrease C-reactive protein concentration.

Metabolic Syndrome is a constellation of endogenous risk factors that increase the risk of development both cardiovascular disease or type 2 diabetes mellitus, therefore there is no specific treatment exclusively for the syndrome. Those people suffering from Metabolic Syndrome generally are treated with a number of different agents, in particular hypoglycemic agents, blood pressure medication, as well as cholesterol lowering drugs. Very often, drug combinations will be necessary to manage multiple risk factors. Several drug combinations have been proposed; such drug combinations are disclosed in the following review of patents, most of them related to the treatment and prevention of the cardiovascular disease resulting from Metabolic Syndrome.

McGovern et al., in U.S. Pat. No. 5,140,012, disclose the use of pravastatin alone or in combination with an angiotensin converting enzyme (ACE) inhibitor, to prevent onset of restenosis following angioplasty. The disclosure is limited to a single inhibitor of HMGCoA, pravastatin and does not includes an antiplatelet agent such as acetylsalicylic.

Liang et al. in U.S. Pat. No. 6,576,256 discloses a combination of a cholesterol lowering agent, a renin angiotensin system inhibitor and the antiplatelet agent aspirin. This invention does not include a hypoglycemic agent.

U.S. Pat. Nos. 5,461,039 and 5,593,971 disclose the use of a cholesterol-lowering drug, alone or in combination with ACE inhibitors, to reduce hypertension in normotensive individuals who have insulin resistance. The disclosed methods are limited to use in normotensive individuals who are insulin-resistant.

Bortolini et al., in U.S. Appl. Pub. No. 2007/0275996, disclose the use of a pharmaceutical composition consisting of a statin for the prevention or treatment of Metabolic Syndrome. A composition consisting of only a lipid lowering agent is not adequate for the treatment of Metabolic Syndrome since Metabolic Syndrome consists of multiple components requiring an specific treatment for each one of these co-morbidities.

Olokatun et al., in U.S. Pat. No. 5,622,985, disclose that HMGCoA inhibitors, particularly pravastatin, when used alone or alternatively in combination with an angiotensin converting enzyme (ACE) inhibitor, decrease the risk of a second heart attack in a patient who has a substantially normal cholesterol level.

Cornett et al., in U.S. Appl. Pub. No. 2006/0154959, claim the use of a formulation comprising a cicletanine (a diuretic drug, usually used in the treatment of hypertension) and a second agent for the treatment of at least one of diabetes, Metabolic Syndrome, dyslipidemia, or complications related to any of these diseases. This patent does not specify which second agent is most suitable, and is restricted to the use of only one agent in addition to cicletanine compositions.

Mexican patent number MX218975 entitled "Composición Farmacéutica que Contiene Estatina y Aspirina" discloses the use of a statin in combination with acetylsalicylic acid to reduce hypercholesterolemia and the risk of myocardial infarction.

Alvarez-Ochoa et al., in Mexican request patent number PA/A/2005/014063, disclose the use of a pharmaceutical composition comprising an antihypertensive and cholesterol lowering compound. The selected hypolipidemic agent and antihypertensive agent were simvastatin and amlodipine, respectively. The disclosure is limited to the use of amlodipine as the antihypertensive agent.

As discussed above, these combinations do not include a hypoglycemic agent, or include hypoglycemic agents which are not suitable for treatment of Metabolic Syndrome (e.g. sulfonylureas or glitazones, which have been shown to promote weight gain). Biguanide metformin is the most suitable hypoglycemic agent to be used in a polypill intended for the treatment and prevention of Metabolic Syndrome since, in addition to its antihyperglycemic effect, it has shown an important effect on reducing the lipid profile, reducing inflammatory state and promoting weight loss.

Only one application (U.S. Appl. Pub. No. 2007/0015839) disclosed the use of metformin in combination with other drugs as an effective method for treating diabetes and Metabolic Syndrome. However, this application comprises a formulation containing two doses of hypoglycemic agent (metformin) to be taken at two different times and a pill containing metformin, simvastatin and a renin-angiotensin system inhibitor. The disadvantage of this application is related to compliance, since individuals who have to take different pills, are less like to do so. Additionally, the use of an antiplatelet agent is optional. In contrast, the lipid lowering agent referred to in the present invention is more powerful and with more pleiotropic effects than simvastatin contained in U.S. Appl. Pub. No. 2007/0015839, giving as a result a most safe and efficacious scheme treatment. The major approaches to manage individuals with Metabolic Syndrome are to reduce most of the underlying causes and to treat hypertension and other cardiometabolic risk factors including hyperglycemia and dyslipidemia individually. Therefore, individuals with Metabolic Syndrome may be required to take five or six different pills, directed at a specific disease, either at once or at different times during the day. Compliance is a critical problem for proper treatment of Metabolic Syndrome. Thus, combining drugs at a lower dose in a single dosage will greatly improve compliance, efficacy and security of the treatment.

BRIEF SUMMARY OF THE INVENTION

The present invention provides a pharmaceutical composition for the treatment of Metabolic Syndrome in mammals, including humans, comprising a therapeutically effective amount of each of at least one cholesterol lowering agent (e.g., atorvastatin, simvastatin, fluvastatin, rosuvastatin, pravastatin), at least one angiotensin converting enzyme inhibitor (e.g., ramipril, enalapril, lisinorpil), at least one antiplatelet agent (e.g., acetylsalicylic acid) and a biguanide hypoglycemic agent (e.g. metformin). In certain embodiments, the invention provides for a pharmaceutical composition comprising ramipril, atorvastatin, metformin and an antiplatelet agent. In further embodiments, the invention provides a pharmaceutical composition comprising ramipril, atorvastatin, metformin and acetylsalicylic acid. In certain embodiments, the invention comprises metformin in an extended release form. In certain pharmaceutical compositions, the present invention can comprise from about 1 mg to about 80 mg, from about 5 mg to about 60 mg, or about 5 mg of ramipril. In certain pharmaceutical compositions, the present invention can comprise from about 5 mg to about 140 mg, from about 20 mg to about 80 mg, or about 20 mg of atorvastatin. In certain pharmaceutical compositions, the present invention can comprise from about 20 mg to about 500 mg, from about 35 mg to about 350 mg, from about 35 to about 100 mg or about 81 mg of acetylsalicylic acid. In certain pharmaceutical compositions, the present invention can comprise from about 100 mg to about 10000 mg, from about 500 mg to about 5000 mg, about 850 mg, or about 500 mg of metformin. The compositions can be in either aqueous solution or solid form and can be administered orally (e.g., capsule, tablet, or powder), parenterally or topically as a single, once daily dose. This combination of drugs in a single daily dosage greatly improves compliance and is more efficacious to treat Metabolic Syndrome.

Other features and advantages of the invention will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. All publications, patent applications, patents, and other references mentioned herein are incorporated by reference in their entirety. In case of conflict, the present specification, including definitions, will control.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described hereinafter.

Definitions

About: As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM, inclusive).

Disease, disorder, condition: As used herein, the terms "disease" or "disorder" refer to any adverse condition of a human or animal including tumors, cancer, allergies, addiction, autoimmunity, infection, poisoning or impairment of optimal mental or bodily function. "Conditions" as used herein includes diseases and disorders but also refers to physiologic states. For example, fertility is a physiologic state but not a disease or disorder; hence, compositions suitable for preventing pregnancy by decreasing fertility would therefore be described herein as a treatment of a condition (fertility), but not a treatment of a disorder or disease. Other conditions encompassed by the use of that term herein will be understood by those of ordinary skill in the art.

Effective Amount: As used herein, the term "effective amount" refers to an amount of a given compound or composition that is necessary or sufficient to realize a desired biologic effect. An effective amount of a given compound or composition in accordance with the methods of the present invention would be the amount that achieves this selected result, and such an amount can be determined as a matter of routine by a person skilled in the art, using assays that are known in the art and/or that are described herein, without the need for undue experimentation. For example, an effective amount for treating or preventing cardiovascular disease could be that amount necessary to prevent the development and/or progression of the symptoms and/or underlying physiological causes of cardiovascular disease, such as hypercholesterolemia and hypertension. The term is also synonymous with "sufficient amount" and "therapeutically effective amount." The effective amount for any particular application can vary depending on such factors as the disease, disorder or condition being treated, the particular composition being administered, the route of administration, the size of the subject, and/or the severity of the disease or condition. One of ordinary skill in the art can determine empirically the effective amount of a particular compound or composition of the present invention, in accordance with the guidance provided herein, without necessitating undue experimentation.

One, a, or an: When the terms "one," "a," or "an" are used in this disclosure, they mean "at least one" or "one or more," unless otherwise indicated. As such, the terms "a" (or "an"), "one or more," and "at least one" can be used interchangeably herein.

Treatment: As used herein, the terms "treatment," "treat," "treated" or "treating" refer to prophylaxis and/or therapy, particularly wherein the object is to prevent or slow down (lessen) an undesired physiological change or disorder, such as the development and/or progression of cardiovascular disease. Beneficial or desired clinical results include, but are not limited to, alleviation of symptoms, diminishment of the extent of disease, stabilized (i.e., not worsening) state of disease, delay or slowing of disease progression, amelioration or palliation of the disease state, and remission (whether partial or total), whether detectable or undetectable. "Treatment" can also mean prolonging survival and/or increased quality of life as compared to expected survival and/or quality of life if not receiving treatment. Those in need of treatment include those already with the condition or disorder (e.g., cardiovascular disease) as well as those prone to have the condition or disorder or those in which the condition or disorder is to be prevented. By "subject" or "individual" or "animal" or "patient" or "mammal," is meant any subject, particularly a mammalian subject, for whom diagnosis, prognosis, or therapy is desired. Mammalian subjects include humans and other primates, domestic animals, farm animals, and zoo, sports, or pet animals such as dogs, cats, guinea pigs, rabbits, rats, mice, horses, donkeys, mules, burros, cattle, cows, and the like.

Overview

The present invention provides pharmaceutical compositions and methods that overcome the limitations of previously reported treatments and methods for treating Metabolic Syndrome. Furthermore, the compositions and methods of the present invention can be useful to manage individuals with Metabolic Syndrome by reducing the underlying causes and treating hypertension and other cardiometabolic risk factors associated with Metabolic Syndrome.

All components of Metabolic Syndrome have adverse effects on the endothelium, thus endothelial dysfunction might be more prevalent in patients with Metabolic Syndrome and could play a role in the increased risk for vascular disease and diabetes mellitus type 2 in this population.

Since Metabolic Syndrome increases the risk of cardiovascular disease, which is mediated by endothelial dysfunction, the composition and methods of the present invention were designed to produce a desirable effect on vascular function and endothelium dependent vasodilation, through modulation of lipoprotein, lipoprotein oxidation, angiotensin physiology, reduction of vascular oxidative stress and reducing insulin resistance thereby reducing cardiometabolic risk factors and the development of cardiovascular disease (CVD).

Atorvastatin, ramipril, metformin and acetylsalicylic acid, which are used in combination in exemplary compositions provided by the present invention, each have different but complimentary mechanisms of action to affect cardiometabolic risk factors.

The compositions and methods provided by the present invention can be used not only for reducing the underlying causes but also for treating the cardiometabolic risk factors of Metabolic Syndrome.

Atherogenic dyslipidemia is a key metabolic risk factor of Metabolic Syndrome. This condition consists of abnormal LDL-C, triglycerides and apoB, and low HDL-C. While not wishing to be bound by any particular theory, it is believed that one of the components of certain exemplary compositions of the present invention, atorvastatin, works in the present compositions and methods by reducing cholesterol synthesis through the inhibition of HMG-CoA reductase. Inhibition of HMG-CoA reductase is known to reduce cholesterol synthesis and improve endothelium-vasomotion in short term treatments. Furthermore, it is believed that lipid lowering treatments down-regulate the angiotensin II type 1 receptor and reduce the release of free radicals. Thus, treatment with atorvastatin protects the vascular endothelium from oxidative damage and reverses the elevated blood pressure, thereby reducing the progression of atherosclerosis and development of cardiovascular disease.

It is also believed that one of the components of the compositions of the present invention, atorvastatin also has an inhibitory effect on vascular superoxide generation and increases human paraoxonase activity (a protective enzyme against LDL-C oxidation). This is in addition to contributing to the reduction in LDL-C cholesterol and is consistent with enhanced nitric oxide (NO) bioactivity. Thus, both mechanisms of action for atorvastatin protect LDL-C from oxidation. Furthermore, atorvastatin may have anti-atherosclerotic effects independent of LDL reduction; for example, atorvastatin treatment can produce a small increase in the anti-artherogenic HDL cholesterol. Thus, atorvastatin has pleiotropic effects on the vascular endothelial architecture: inhibition of smooth muscle cell proliferation, reduction of matrix metalloproteinase expression, and stimulation of the antithrombotic system.

Because cardiovascular risk is high in hypertensive patients with Metabolic Syndrome, it is advisable to pursue rigorous blood pressure control to lower blood pressure to values less than the high ones that are a common component of the syndrome. Several pathophysiology factors are involved in the relationship between hypertension and the other components of Metabolic Syndrome, including inappropriate activation of the renin-angiotensin-aldosterone system, oxidative stress and inflammation.

Similarly, while not wishing to be bound by any particular theory, it is believed that another of the components of certain exemplary compositions of the present invention, ramipril, works in the present compositions and methods to reduce angiotensin II formation by inhibiting the angiotensin II converting enzyme. Ramipril is known to reduce bradykinin degradation and diminish intracellular production of superoxide anions thus protecting LDL cholesterol from oxidation and thereby improving endothelial function. A reduction in bradykinin degradation augments NO (Nitric Oxide) bioactivity with activation of endothelial B2 kinin receptors and stimulation of NO synthase activity. The vasodilating properties of NO contribute to the antihypertensive effect of ramipril. ACE inhibition also diminishes intracellular production of superoxide anions via reduced activity of angiotensin II-dependent oxidases in the endothelium and vascular smooth muscle, thus protecting NO from oxidant degradation to biologically inert or toxic molecules. Inhibition of the production of superoxide anions also limits the oxidation of LDL, thus contributing to an increase in NO bioactivity by enhancing NO synthesis and limiting oxidative degradation of NO. Ramipril thus prevents LDL from oxidation and attenuates atherosclerosis. In this way, it is believed that ramipril promotes the diminishment of intracellular production of superoxide anions protecting LDL cholesterol from oxidation and reduces bradykinin degradation, thus improving overall vascular endothelium function. In addition to the benefits of lowering blood pressure and attenuation of atherosclerosis, ramipril also decreases intraglomerular pressure and glomerular membrane permeability to albumin, therefore contributing to decreased microalbuminuria, another risk factor of cardiovascular disease. Ramipril also improves insulin sensitivity and glycemic control which contributes to a reduction in the incidence of new onset of type 2 diabetes.

Patients with Metabolic Syndrome exhibit a higher platelet activity that may provide a pathophysiological link between platelets and adverse thrombotic events. Antiplatelet drugs are an important pharmacological tool for treatment and prevention of Metabolic Syndrome, as well as an adjunct therapy for these patients.

Likewise, while not wishing to be bound by any particular theory, it is believed that one of the components of certain exemplary compositions of the present invention, acetylsalicylic acid, works to reduce the activation and aggregation of platelets by inhibiting cyclooxygenases (COX-1 and COX-2) and the formation of thromboxane. In this way, it is believed that acetylsalicylic acid reduces the release of inflammatory cytokines at the site of vascular endothelial injury thus attenuating major vascular events.

Insulin resistance is a key feature of Metabolic Syndrome and plays an important role in the pathogenesis of endothelial dysfunction. Hyperinsulinaemia and insulin resistance are associated with an impaired NO release from endothelial cells and with reduced endothelial function. Therefore, it is believed that one of the components of certain exemplary compositions of the present invention, metformin, an insulin sensitizing biguanide, improves not only insulin sensitivity in liver and muscle, as its primary anti-hyperglycemic mechanism of action, but also induces additional beneficial effects on several metabolic abnormalities associated with Metabolic Syndrome which benefit endothelial function such as weight loss and reduction of lipid concentration in blood.

Likewise, while not wishing to be bound by any particular theory, it is believed that a combination of the components of the compositions of the present invention, acetylsalicylic acid and atorvastatin, have an additional positive effect on CVD development and progression via a reduction of vascular oxidative stress. Acetylsalicylic acid is believed to inhibit the expression of the lectin-like receptor LOX-1 that is induced by oxidized low density lipoprotein in endothelial cells. This inhibition is associated with a reduction of the expression of matrixmetalloproteinase I. The inhibitory effect of acetylsalicylic acid in the expression of lectin-like receptor and matrixmetalloproteinases-1 improves endothelial NO bioavailability, protecting endothelial cells from vascular oxidative stress. As discussed herein, a reduction in NO bioavailability increases vascular oxidative stress thus promoting the atherosclerotic process. Statin treatment, such as with atorvastatin, is known to reduce platelet aggregation, possibly via reduction of thromboxane A2 production and cholesterol content of platelet membranes, and is known to reduce thrombogenic potential, via an effect on tissue factor (also called platelet tissue factor, factor III, thrombokinase, or CD142 is a protein present in subendothelial tissue, platelets, and leukocytes necessary for the initiation of thrombin formation from the zymogen prothrombin). Thus, the combination of acetylsalicylic acid and atorvastatin has a synergistic effect in reducing atherothrombotic risk.

Hypercholesterolemia, an increase in LDL-C oxidation and an increase in angiotensin II degradation have been identified as some of the most important promoters of the vascular endothelial damage. Therefore, while not wishing to be bound by any particular theory, it is believed that a combination of the components of the present invention, ramipril and atorvastatin, have an additional positive effect on endothelial function. Ramipril works in the present compositions and methods to reduce angiotensin II formation by inhibiting the angiotensin converting enzyme reducing intracellular production of superoxide anions thus protecting LDL cholesterol from oxidation and improving endothelial function. Atorvastatin works in the present compositions by inhibiting HMG-CoA reductase. Inhibition of HMG-CoA reductase is known to reduce cholesterol synthesis and improve endothelium-vasomotion in short term treatments. Furthermore, it is believed that lipid lowering treatments down-regulate the angiotensin II type 1 receptor and reduce the release of free radicals. Thus, both atorvastatin and ramipril protect the vascular endothelium from oxidative damage and reverse elevated blood pressure, thereby reducing the progression of atherosclerosis and development of cardiovascular disease.

In addition to dyslipidemia, hypertension and hyperglycemia, individuals with Metabolic Syndrome have other physiological characteristics such as chronic systemic inflammation. C-reactive protein and interleukins are the most studied inflammatory markers. Therefore, while not wishing to be bound by any particular theory, it is believed that a combination of the atorvastatin and metformin, have an additional positive effect on inflammatory markers, in addition to their known effects on glucose and metabolism lipids.

Likewise, while not wishing to be bound by any particular theory, it is believed that a combination of the components of the compositions of the present invention, metformin and ramipril, have an additional positive effect on CVD development via reduction of insulin resistance and improvement of endothelial function. Metformin improves insulin sensitivity, reduces weight loss, reduces plasma glucose and plasma lipid concentrations, while ramipril not only improves blood pressure, but also has beneficial impact on inflammation, oxidative stress, insulin sensitivity and glucose homeostasis complementing the effect of metformin.

The combination of metformin, ramipril, atorvastatin and acetylsalicylic acid is particularly effective in treating Metabolic Syndrome, the combination is complementary and acts synergistically to have an increased benefit in patients with Metabolic Syndrome. Biguanide metformin is normally administered in large dosages, twice or three times a day. Thus, administering one day's dosage in combination with other drugs in a pill may be difficult. This issue has been addressed by adding the biguanide bound to a polymer which produces extended release form of metformin allowing its use together with the other drugs of the composition in a single dosage form at low dose. This combination of drugs in a single daily dosage aside from being more effective, also increases compliance, which is a critical factor for successful treatment of patients with Metabolic Syndrome.

Compositions

In one embodiment, the present invention provides pharmaceutical compositions useful to treat individuals with Metabolic Syndrome, reducing the underlying causes and treating hypertension and other cardiometabolic risk factors.

Exemplary pharmaceutical compositions according to this aspect of the invention comprise a therapeutically effective amount of each of at least one cholesterol lowering agent, at least one angiotensin converting enzyme inhibitor, at least one anti-hyperglycemic agent and at least one antiplatelet agent. By "at least one" such agent is meant that one or more (e.g., one, two, three, four, five, etc.) of each of these agents may be present in combination in the composition of the present invention, but at least one of each of the respective classes of agents must be present in the same composition.

In certain embodiments, the invention provides pharmaceutical compositions for the treatment of Metabolic Syndrome and its cardiometabolic risk factors, comprising a therapeutically effective amount of at least one angiotensin converting enzyme inhibitor. Examples of angiotensin converting enzyme inhibitors suitable for use in the compositions of the invention comprise, but are not limited to captopril, enalapril, lisinopril, benazapril, fosinopril, quinapril, ramipril, spirapril, imidapril, and moexipril. Other suitable angiotensin converting enzyme inhibitors that can be advantageously used in the compositions of the present invention will be familiar to one of ordinary skill. In particular compositions, the angiotensin converting enzyme inhibitor is ramipril.

In certain such embodiments, an angiotensin converting enzyme inhibitor is present in the pharmaceutical compositions of the invention in an amount from about 1 mg to about 80 mg of an angiotensin converting enzyme inhibitor. In other embodiments, the angiotensin converting enzyme inhibitor is present in the compositions in an amount from about 5 mg to about 60 mg. In specific embodiments, ramipril is present in the compositions in an amount of about 5 mg.

In certain embodiments, the invention provides pharmaceutical compositions for the treatment of Metabolic Syndrome and its cardiometabolic risk factors, comprising a therapeutically effective amount of at least one angiotensin receptor blocker. Suitable angiotensin receptor blockers can be selected from the group comprising losartan, irbesartan, valsartan, among others.

In certain embodiments, the invention provides pharmaceutical compositions for the treatment of Metabolic Syndrome and its cardiometabolic risk factors, comprising a therapeutically effective amount of at least one cholesterol lowering agent. Examples of cholesterol lowering agents suitable for use in the compositions of the invention comprise, but are not limited to, statins, fibrates, niacins and derivatives thereof, and bile acid sequestrants. Other suitable cholesterol lowering agents that can be advantageously used in the compositions of the present invention will be familiar to one of ordinary skill. In particular methods, the cholesterol lowering agent is atorvastatin. In certain such embodiments, the cholesterol lowering agent is present in the pharmaceutical compositions in an amount from about 5 mg to about 140 mg of cholesterol lowering agent. In other embodiments, the cholesterol lowering agent is present in the compositions in an amount from about 20 mg to about 80 mg. In specific embodiments, atorvastatin is present in the compositions in an amount of about 20 mg.

In certain embodiments, the invention provides pharmaceutical compositions for the treatment of Metabolic Syndrome and its cardiometabolic risk factors, comprising a therapeutically effective amount of at least one antiplatelet agent. Examples of antiplatelet agents suitable for use in the compositions of the invention comprise, but are not limited to, cyclooxygenase inhibitors, adenosine diphosphate (ADP) receptor inhibitors, phosphodiesterase inhibitors, glycoprotein inhibitors, and adenosine reuptake inhibitors. Other suitable antiplatelet agents that can be advantageously used in the compositions of the present invention will be familiar to one of ordinary skill. Antiplatelet agent is selected from the group comprised of acetylsalicylic acid, warfarin, ticlopidine, clopidogrel, dypyridamole, among others. In particular compositions, the antiplatelet agent is acetylsalicylic acid. In certain such embodiments, an antiplatelet agent is present in the pharmaceutical compositions in an amount from about 20 mg to about 500 mg of an antiplatelet agent. In other embodiments, the antiplatelet agent is present in the compositions in an amount from about 35 mg to about 350 mg. In other embodiments, the antiplatelet agent is present in the compositions in an amount from about 35 mg to about 100 mg. In specific embodiments, acetylsalicylic acid is present in the compositions in an amount of about 81 mg.

In certain embodiments, the invention provides pharmaceutical compositions for the treatment of Metabolic Syndrome and its cardiometabolic risk factors, comprising a therapeutically effective amount of at least one anti-hyperglycemic agent. Examples of anti-hyperglycemic suitable for use in the compositions of the invention comprise, but are not limited to, metformin, pioglitazone, glimepiride, rosiglitazone, glibenclamide and acarbose. Other suitable anti-hyperglycemic agents that can be advantageously used in the compositions of the present invention will be familiar to one of ordinary skill. In particular methods, the anti-hyperglycemic agent is the biguanide metformin. In certain such embodiments the biguanide metformin is present in the pharmaceutical composition in extended release form. In certain such embodiments, the anti-hyperglycemic agent metformin is present in the pharmaceutical compositions in an amount from about 100 mg to about 10000 mg. In other embodiments, the anti-hyperglycemic agent metformin is present in the compositions in an amount from about 500 mg to about 5000 mg. In specific embodiments, metformin is present in the compositions in an amount of about 850 mg. In specific embodiments, metformin is present in the compositions in an amount of about 500 mg.

The pharmaceutical compositions of the invention may be administered by any means that achieves their intended purpose. For example, administration may be by parenteral, subcutaneous, intravenous, intramuscular, intradermal, intraperitoneal, transdermal, buccal, sublingual, intrathecal, intracranial, intranasal, ocular, pulmonary (e.g., via inhalation) or topical routes. Alternatively, or concurrently, administration may be by the oral route. The dosage administered will be dependent upon the age, health, and weight of the recipient, kind of concurrent treatment, if any, frequency of treatment, and the nature of the effect desired.

Suitable oral pharmaceutical compositions of the present invention are manufactured in a manner which is itself well-known in the art, for example, by means of conventional mixing, granulating, dragee-making, dissolving, or lyophilizing processes. Thus, solid pharmaceutical preparations for oral use can be obtained by combining a pharmaceutical composition of the invention and optionally one or more additional active pharmaceutical ingredients with one or more solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose, sucrose, fructose and the like; sugar alcohols such as mannitol, sorbitol, or xylitol and the like; cellulose preparations and/or calcium phosphates, for example tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or poly (ethylene glycol). Dragee cores are provided with suitable coatings which, if desired, are resistant to gastric juices. For this purpose, concentrated saccharide solutions may be used, which may optionally contain gam arabic, talc, polyvinyl pyrrolidone, poly(ethylene glycol) and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, can be used. Dye stuffs or pigments may be added to the tablets or dragee coatings, for example, for identification or in order to characterize combinations of active ingredients or doses thereof.

Other pharmaceutical preparations which can be used orally include push-fit capsules made of gelatin, as well as soft, sealed capsules made of gelatin and a plasticizer such as glycerol or sorbitol. In certain embodiments, the push-fit capsules can comprise a pharmaceutical composition of the invention in the form of granules which may be mixed with fillers such as lactose, binders such as starches, and/or lubricants such as talc or magnesium stearate and, optionally, stabilizers. In soft capsules, one or more pharmaceutical ingredients (e.g., a pharmaceutical composition of the invention and optionally one or more additional active pharmaceutical ingredients) are preferably dissolved or suspended in suitable liquids, such as fatty oils, or liquid paraffin. In addition, stabilizers may be added.

Suitable pharmaceutical preparations which can be used rectally include, for example, suppositories, which comprise a combination a pharmaceutical composition of the invention with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, poly(ethylene glycols), or paraffin hydrocarbons.

In addition to the solid dosage forms disclosed throughout, the present invention also provides chewable oral formulations. In certain such embodiments, the formulations will comprise (or consist essentially of) an effective amount of a pharmaceutical composition of the invention along with suitable excipients that allow the formulations to be chewed by the patient. In additional embodiments, the formulations can further comprise one or more taste-masking or sweetening agents, such as those described herein. In one embodiment, sucralose is used in the chewable formulations. Additional active agents, such as those described herein, can also optionally be added to the chewable formulations. The amount of a pharmaceutical composition of the invention, other optional active agents and sweetening agents (e.g., sucralose) in the chewable formulations of the present invention are readily determinable by those of ordinary skill in the art, and include those amounts and combinations described herein. For example, the chewable formulations of the present invention comprise (or consist essentially of) a pharmaceutical composition of the invention and about 0.05% to about 0.15% sucralose. Such chewable formulations are especially useful in patient populations where compliance is an issue, such as children, the elderly, and patients who may have difficulty swallowing or using spray/inhalable formulations.

The formulations may also contain colorants to improve the appearance of the chewable formulations, especially since an attractive coloration imparted by a colorant may improve patient compliance. The relative amounts of the colorants selected will vary depending upon the particular hue of the individual colorants and the resultant color desired.

Any standard pharmaceutically acceptable excipient can be used in the chewable tablet formulations which provides adequate compression such as diluents (e.g., mannitol, xylitol, maltitol, lactitol, sorbitol, lactose, sucrose, and compressible sugars such as DiPac® (dextrinized sucrose), available from Austin Products Inc. (Holmdel, N.J.), binders, disintegrants, splitting or swelling agents (e.g., polyvinyl polypyrrolidone, croscarmellose sodium (e.g., Ac-Di-Sol available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, (Philadelphia, Pa.), lubricating agents (e.g., magnesium stearate), and flow agents (e.g., colloidal silicon dioxide, such as Cab-O-Sil M5® available from Cabot Corporation, Kokomo, Ind.).

Suitable amounts of sweetener (e.g., sucralose) used in the chewable formulations, will be familiar to, and can be readily determined by, those skilled in the art. In certain embodiments, the sweetener is present in an amount from about 0.05% to about 5.0% (e.g., about 0.05%, about 0.1%, about 0.125%, about 0.15%, about 0.2%, about 0.3%, about 0.4%, about 0.5%, about 0.6%, about 0.7%, about 0.8%, about 0.9%, about 1%, about 1.25% about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75% or about 5%). Those or ordinary skill in the art will appreciate that the amount of sweetener may vary depending on the strength of the particular sweetener used and the levels approved by the regulatory authorities for use in pharmaceutical products.

Suitable cyclodextrins for use in the chewable formulations of the present invention include α, β, or γ cyclodextrins, or an alkylated or hydroxyalkylated derivatives thereof, such as heptakis (2,6-di-o-methyl)-β-cyclodextrin (DIMEB), randomly methylated β-cyclodextrin (RAMEB), and hydroxypropyl β-cyclodextrin (HPβCD). A suitable cyclodextrin is β-cyclodextrin (available from Cerestar USA, Inc., Hammond, Ind. or from Roquette America, Inc., Keokuk. Iowa under the trade name Kleptose™). If desired, the complex of the active substance with cyclodextrin can be prepared in advance, for example, by malaxating or granulating a pharmaceutical composition of the invention and any additional active substance(s) and the cyclodextrin in the presence of water, or by preparing an aqueous solution containing a pharmaceutical composition of the invention and any additional active substance(s) and the cyclodextrin in the desired molar ratio. Alternatively, the pharmaceutical composition of the invention and any additional active substance(s) and the cyclodextrin can be simply mixed with other excipients and adjuvants.

A typical manufacturing process for making either a single layer or multi-layer chewable tablet generally involves blending of the desired ingredients to form a uniform distribution of the pharmaceutical composition of the invention (and any other active agent(s)), excipients (e.g., colorants and flavoring agents as well as others). If desired, an inclusion complex of a pharmaceutical composition of the invention and any other active agent(s) and cyclodextrin (e.g., β-cyclodextrin) may be formed prior to blending into the mixture by malaxating a pharmaceutical composition of the invention and any other active agent(s) and cyclodextrin in the presence of water in a planetary mixer for about 20 minutes. The mixture is then dried in a drying oven. After drying, the complex is mixed with any color/flavoring blend. The blend is then compressed into a single layer or multi-layer tablet using standard methods well-known to those skilled in the art (e.g., Kilian T-100 tablet press or Courtoy 292/43 rotary bi-layer press). The colorants and flavoring agents may be added to both layers to form a uniform presentation of the tablet. Methods for preparation of chewable tablets and various components for use in the tablets can be found throughout the detailed description section and the Examples of U.S. Patent Publication No. 2003/0215503, the disclosure of which is incorporated by reference herein for all purposes. Additional chewable/orally dissolving tablets, and methods for their manufacture, are disclosed in U.S. Patent Publication No. 2004/0265372 and U.S. Pat. No. 6,270,790, the disclosures of each of which are incorporated by reference herein for all purposes.

In another embodiment, the present invention provides orally disintegrating/orodispersible tablets, such as those disclosed in U.S. Pat. No. 6,723,348, the disclosure of which is incorporated herein by reference in its entirety for all purposes. The orally disintegrating/orodispersible tablets suitably disintegrate in the buccal cavity upon contact with saliva forming an easy-to-swallow suspension. Such tablets comprise a pharmaceutical composition of the invention, and optionally, one or more additional active agents (such as those described herein), in the form of coated granules, and a mixture of excipients comprising at least one disintegrating agent, a soluble diluent agent, a lubricant and optionally a swelling agent, an antistatic (fluid flow) agent, a permeabilising agent, sweeteners, flavoring agents and colors.

In other suitable embodiments, the particles/granules of compositions of the invention (and any other optional active agents) have a particle size such that about 100% of the particles have an average size of less than about 50 μm. In suitable such embodiments, a pharmaceutical composition of the invention (and any other optional active agents) are present as coated granules.

In one embodiment, disintegrating tablets according to this aspect of the invention comprise coated granules of compositions of the invention and a mixture of excipients, the ratio of the mixture of excipients to the coated granules suitably is about 0.4:1 to about 9:1, more suitable about 1.5:1 to about 5:1, or about 2 to 3 parts by weight, the mixture of excipients suitably comprising: at least one disintegrating agent, a soluble diluent agent, a lubricant, and optionally a permeabilising agent, a swelling agent, an antistatic agent, flavoring agents and one or more coloring agents.

In suitable embodiments, the disintegrating agent is selected from the group consisting of croscarmellose, available as e.g. Ac-di-sol™, crospovidone available as e.g. Kollidon CL™, sodium starch glycolate and mixtures thereof.

According to one embodiment of the invention, the soluble diluent is a polyol having less than 13 carbon atoms and being either in the form of a directly compressible product with an average particle size of about 100 to 500 µm, or in the form of a powder with an average particle size of less than about 100 µm, this polyol suitably being selected from the group consisting of mannitol, xylitol, sorbitol and maltitol. The proportion of disintegrating agent suitably is from about 3 to about 15% by weight, e.g., about 5 to about 15% by weight, and in the case of a mixture, each disintegrating agent being present between about 1 and about 10% by weight, e.g., about 5 to about 10% by weight, and the proportion of soluble diluent agent being about 30 to about 90% by weight, e.g., about 40 to about 60% by weight, based in each case on the weight of the tablet.

Suitable lubricants for use in the disintegrating tablets include, but are not limited to, magnesium stearate, stearic acid, sodium stearyl fumarate, micronised polyoxyethyleneglycol (micronised Macrogol 6000), leukine, sodium benzoate and mixtures thereof. The amount of lubricant generally is from about 0 to about 3%, e.g., from about 1 to about 2% by weight, based on the weight of the tablet. The lubricant can be dispersed within the mixture of excipients, or according to one embodiment, sprayed over the outer surface of the tablet. Thus, according to one embodiment of the disintegrating tablets of the invention, the lubricant is in powder form and is, at least in part, disposed on the surface of the tablets.

The permeabilising agent allows the creation of a hydrophilic network which facilitates the penetration of saliva and hence assists the disintegration of the tablet. Suitable permeabilising agent include, but are not limited to, silica with a high affinity for aqueous solvents, such as colloidal silica (Aerosil™), precipitated silica (Syloid™ FP 244), maltodextrins, β-cyclodextrins and mixtures thereof. The amount of permeabilising agent suitably is between about 0 and about 5%, e.g., from about 0.5 to about 2% by weight, based on the weight of the tablet.

A swelling agent can be incorporated in the mixture of excipients. Suitable swelling agents include, but are not limited to, starch, modified starch or microcrystalline cellulose.

An antistatic agent can also be incorporated as a flow aid. Suitable antistatic agents include, but are not limited to, micronised or non-micronised talc, fumed silica (Aerosil™ R972), colloidal silica (Aerosil™ 200), precipitated silica (Syloid™ FP 244), and mixtures thereof.

According to one such embodiment of the invention, the granules of the compositions of the invention are characterized in that the granules are coated and comprise microcrystals of composition(s) of the invention, at least one binder, and optionally a diluent agent, an antistatic agent, and a coloring agent. Furthermore, the granulation excipients can also include disintegrating agents and/or surfactants.

Suitable binders include, but are not limited to, cellulosic polymers, such as ethylcellulose, hydroxypropylcellulose and hydroxypropylmethyl cellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, sucrose and its derivatives, guar gum, poly(ethylene glycol), for example an acrylic polymer, such as Eudragit™ E100, and mixtures thereof.

Optionally, in order to enhance the granulation of the composition(s) of the invention a diluent agent can be used. Suitable diluent agents include, but are not limited to, microcrystalline cellulose, sucrose, dicalcium phosphate, starches, lactose and polyols of less than 13 carbon atoms, such as mannitol, xylitol, sorbitol, maltitol, pharmaceutically acceptable amino acids, such as glycin, and their mixtures.

In one embodiment, a granule of one or more of the composition(s) of the invention, can be in the form of a core of granulated microcrystals of one or more compositions of the invention, coated with at least one layer comprising a composition of the invention. Such a coated core is characterized in that the core and the layer comprise each from 70% to 95%, preferably 80% to 95% by weight of one or more compositions of the invention, the balance to 100% being formed with at least one binder and optionally sucralose, and that the coated core is suitably a sphere. See e.g., French patent application FR 00 14803, the disclosure of which is incorporated by reference herein.

The granules can also be coated with a coating composition comprising at least one coating polymer selected from the group consisting of cellulosic polymers, acrylic polymers and their mixtures. Among the cellulosic polymers, ethylcellulose, hydroxypropylcellulose (HPC) and hydroxypropylmethylcellulose (HPMC), can be used. Among the acrylic polymers, insoluble acrylate ammonio-methacrylate copolymer (Eudragit™ RL100 or RS100 or Eudragit™ RL30D or RS30D), polyacrylate (Eudragit™NE30D), or methacrylic copolymers (e.g., Eudragit™ L100-55 Eudragit™ L30D, Eudragit™ E100 and Eudragit™ EPO) can be used, alone, in combination, or in admixture with pH-dependent polymers. Eudragit™ E100 or a mixture of Eudragit™ EPO and Eudragit™ NE30D are suitably used. In one embodiment, the binder and the coating polymer are the same polymer.

Optionally, permeabilising agents, plasticizers, soluble agents, disintegrating agents and surfactants, can be added as coating additives. Suitable plasticizers include, but are not limited to, triacetine, triethylacetate, triethylcitrate (Eudraflex™), ethylphthalate, or mixtures thereof. The plasticizer is used in proportions of at most about 30%, preferably 10% by weight of the coating polymers. Suitable soluble agents include polyols having less than 13 carbon atoms. Surfactants may be an anionic, nonionic, cationic, zwitterionic or amphoteric surfactant. Suitable disintegrating agents include, but are not limited to, croscarmellose, available as e.g. Ac-di-sol™, crospovidone available as e.g. Kollidon CL™, and mixtures thereof.

Suitably, the coated granules according to the present invention have a particle size distribution between about 150 µm and about 500 µm, more suitably between about 150 µm and about 425 µM, such that at least 50%, more suitably at least 70% of the granules have a particle size ranging between about 150 and about 425 µm, and less than 15% of the granules have a particle size less than about 150 µm.

In one embodiment, the coated granules according to the invention comprise: from about 10% to about 95%, preferably about 40 to about 75% of granules of a composition of the invention and optionally one or more optional additional active agents, such as those disclosed herein, sucralose from about 0.05% to about 5%, from about 5 to about 90%, suitably about 10 to about 70% and even more suitably from about 25 to about 55% of a coating polymer, such as Eudragit™ E100, the percentages being expressed by weight relative to the weight of the granules of a composition of the invention, from about 0 to about 10% of a permeabilising agent, such as colloidal silica, the percentages being expressed by weight relative to the weight of the coating polymer.

In another embodiment, the present invention provides solid, effervescent, rapidly dissolving dosage forms, such as those disclosed in U.S. Pat. No. 6,245,353, the disclosure of which is incorporated herein by reference in its entirety. The effervescent, rapidly dissolving dosage forms suitably comprise one or more pharmaceutical compositions of the present invention. Such effervescent dosage forms can further comprise (a) an effervescent base comprising at least one of (i) at least one of (1) an organic edible acid and (2) a salt thereof, (ii) at least one of an alkali metal and an alkaline earth metal carbonate and bicarbonate. In certain other embodiments, the effervescent dosage form of the present invention can further comprise a pharmaceutically acceptable auxiliary ingredient.

In use of such effervescent dosage forms of the present invention, a solution or suspension of a composition of the invention is formed by adding water to the soluble or dispersible effervescent tablets or soluble granules, with evolution of $CO_2$ gas. The resulting effervescent solution or suspension can be ingested very easily, even by patients who have difficulties swallowing. The rapidly disintegrating tablet can also be administered so that it directly disintegrates in the mouth. A rapid release of the active ingredients or compositions is of particular importance here, to ensure a rapid onset of action.

Effervescent agents capable of releasing $CO_2$, which can be used in the present invention, include alkali metal carbonates or alkali metal bicarbonates, such as sodium carbonate or sodium bicarbonate. Agents for inducing $CO_2$ release which are suitably employed are edible organic acids, or their acidic salts, which are present in solid form and which can be formulated with the one or more compositions of the invention and the other auxiliary ingredients (as well as any other active agents) to provide granules or tablets, without premature evolution of $CO_2$. Edible organic acids which can be so used include for example, tartaric acid, malic acid, fumaric acid, adipic acid, succinic acid, ascorbic acid, maleic acid or citric acid. Pharmaceutically acceptable acidic salts include, for example, salts of polybasic acids which are present in solid form and in which at least one acid function is still present, such as sodium dihydrogen or disodium hydrogen phosphate or monosodium or disodium citrate.

In one such embodiment, the present invention thus provides effervescent formulations of one or more compositions of the invention including the formulations and compositions described herein, having an effervescent base comprising (a) a mixture of calcium carbonate with an organic edible acid; (b) a mixture of calcium carbonate, sodium carbonate, sodium bicarbonate and an organic edible acid; or (c) a mixture of sodium bicarbonates, sodium carbonate and an organic edible acid.

Exemplary soluble or dispersible effervescent tablets suitably comprise one or more compositions of the invention, a suitable amount of an effervescent base, and excipients. The effervescent base suitably comprises from about 100 mg to about 500 mg calcium ions as, for example, calcium carbonate, and from about 20 mg to about 1500 mg citric acid and/or its salts. In another embodiment, the effervescent base comprises from about 50 mg to about 2000 mg sodium bicarbonate, from about 20 mg to about 200 mg of sodium carbonate and from about 20 mg to about 1500 mg citric acid and/or from about 20 mg to about 500 mg tartaric acid. An additional suitable composition of the effervescent base comprises from about 50 mg to about 500 mg sodium bicarbonate, from about 20 mg to about 100 mg sodium carbonate, and from about 50 mg to about 750 mg calcium carbonate and from about 100 mg to about 1500 mg of citric acid.

The soluble/dispersible tablets can be prepared by known processes for preparing effervescent bases, such as those disclosed in U.S. Pat. No. 6,245,353, the disclosure of which is incorporated herein by reference in its entirety.

Another embodiment of the present invention provides a physiologically acceptable film that is particularly well-adapted to dissolve in the oral cavity of a warm-blooded animal including humans, and adhere to the mucosa of the oral cavity, to allow delivery of a pharmaceutical composition of the invention. Such physiologically acceptable films suitable for use in accordance with this aspect of the present invention are disclosed in U.S. Patent Application No. 2004/0247648, the disclosure of which is incorporated herein by reference in its entirety.

In one such embodiment of the present invention, an orally dissolving/consumable film comprises a modified starch, a pharmaceutical composition of the invention and optionally at least one water soluble polymer. The amount of a pharmaceutical composition of the invention present in such formulations is readily determinable by those of ordinary skill in the art, and include those amounts and combinations described herein.

The consumable films according to this aspect of the present invention may comprise one or more of the following ingredients: water, antimicrobial agents, additional film forming agents or water soluble polymers, plasticizing agents, flavorings, sulfur precipitating agents, saliva stimulating agents, cooling agents, surfactants, stabilizing agents, emulsifying agents, thickening agents, binding agents, coloring agents, triglycerides, poly(ethylene) oxides, propylene glycols, or sweeteners, fragrances, preservatives and the like, as described in U.S. Pat. No. 6,596,298, the disclosure of which is incorporated by reference herein in its entirety.

In one such embodiment, the consumable films of the present invention include a modified starch. The modified starches used in accordance with the present invention can be prepared by mechanically, chemically or thermally modifying unmodified starches. For example, modified starches may be prepared by chemically treating starches to produce, for example, acid treatment starches, enzyme treatment starches, oxidized starches, cross-bonding starches, and other starch derivatives. Starches suitable for modification to produce modified starches may be obtained from natural products such as corn, potatoes, tapioca as well as genetically modified forms of the same such as high amylose and waxy corn as well as sorghum varieties.

Examples of modified starches for use in the practice of the present invention include, but are not limited to, modified corn starches, modified tapioca starches, acid and enzyme hydrolyzed corn and/or potato starches, hypochlorite-oxidized starches, acid-thinned starches, ethylated starches, cross-bonded starches, hydroxypropylated tapioca starches, hydroxypropylated corn starches, pregelatinized modified starches, and the like. Preferred modified starches are selected from pregelatinized modified corn starches and pregelatinized modified tapioca starches.

Representative examples of commercially available modified starches useful in the present invention include PURE-COTE™ modified starches such as PURE-COTE™ B793 (a pregelatinized modified corn starch) and PURE-COTE™ B795 (a pregelatinized modified corn starch), for example, available from Grain Processing Corporation, 1600 Oregon Street, Muscatine, Iowa 52761-1494 USA.

In one such embodiment of the present invention, the modified starch is present in amounts ranging from about 1% to about 90% by weight, in another embodiment about 10% to about 90% by weight, and in yet another embodiment from about 35% to about 80% by weight of the film.

Modified starch may be included in the film alone or optionally in combination with an additional water soluble film forming polymers such as those selected from, for example, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, poly(ethylene glycol), tragacanth gum, guar gum, acacia gum, arabic gum, polyacrylic acid, methylmethacrylate copolymers, carboxyvinyl polymers, amylose, high amylose starch, hydroxypropylated high amylose starch, pectin, dextrin, chitin, chitosan, levan, elsinan, collagen, gelatin, zein, gluten, soy protein isolate, whey protein isolate, casein and combinations thereof. A preferred water soluble polymer is pullulan. The amount of the water soluble polymer typically is up to about 99% by weight, suitably up to about 80% by weight, more suitably up to about 50% by weight, and most suitably up to about 40% by weight of the film Suitable formulations for oral and/or parenteral administration include aqueous solutions of one or more pharmaceutical compositions of the invention, in water-soluble form, for example, water-soluble salts and alkaline solutions. In addition, suspensions of the active ingredient(s) as appropriate oily injection suspensions may be administered. Suitable lipophilic solvents or vehicles include fatty oils, for example, sesame oil, or synthetic fatty acid esters, for example, ethyl oleate or triglycerides or poly(ethylene glycol)-400. Aqueous injection suspensions may optionally also comprise substances which increase the viscosity of the suspension including, for example, sodium carboxymethyl cellulose, sorbitol, and/or dextran. Optionally, the suspension may also contain one or more stabilizers, one or more preservatives (e.g., sodium edetate, benzalkonium chloride, and the like), and/or other components commonly used in formulating pharmaceutical compositions.

Suitable topical pharmaceutical compositions of the invention are formulated preferably as oils, creams, lotions, ointments and the like by choice of appropriate carriers. Exemplary compositions according to this aspect of the invention therefore comprise one or more pharmaceutical compositions of the invention, and one or more carriers suitable for use in preparing such pharmaceutical compositions for topical administration. Suitable such carriers include vegetable or mineral oils, white petrolatum (white soft paraffin), branched chain fats or oils, animal fats and high molecular weight alcohol (greater than C12). The preferred carriers are those in which the active pharmaceutical ingredient(s) are soluble. Emulsifiers, stabilizers, humectants and antioxidants may also be included, as well as agents imparting color or fragrance, if desired. Additionally, one or more transdermal penetration enhancers can be employed in these topical formulations. Non-limiting examples of suitable such enhancers can be found in U.S. Pat. Nos. 3,989,816 and 4,444,762, which are incorporated be reference herein in their relevant parts.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of one or more of compositions of the present invention in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving one or more of compositions of the present inventions in a suitable high molecular weight alcohol such as propylene glycol or poly(ethylene glycol).

Liquid dosage forms for oral administration include pharmaceutically acceptable emulsions, solutions, suspensions, syrups and elixirs. In addition to one or more pharmaceutical compositions of the invention, liquid dosage forms may contain inert diluents and/or solvents commonly used in the art. Water is the solvent of choice for the formulations of the invention; however, combinations of water with other physiologically acceptable solvents as required are also satisfactory for use. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as poly(ethylene glycols), and surfactants/emulsifiers like the fatty acid esters of sorbitan, and mixtures thereof. Oils, in particular, cottonseed, peanut, or corn oils, may also be added to the compositions. The combination of the additional solvents in the aqueous solution should preferably not exceed about 15% (w/v) of the total composition. Besides inert diluents, the oral compositions can also include adjuvants such as wetting agents, emulsifying and suspending agents (e.g., microcrystalline cellulose, sodium carboxymethyl cellulose, hypromellose, carbopol and the like), surfactants, sweetening, flavoring, and perfuming agents, including those described in further detail herein below. Liquid dosage forms that provide the active ingredients or compositions of the invention in suspension may comprise, in addition to a pharmaceutical composition of the invention, one or more suspending agents such as microcrystalline cellulose, magnesium aluminum silicate, bentonite, agar-agar, hypromellose, sodium carboxymethyl cellulose, carbopol/carbomer, pectin, acacia, tragacanth or their mixtures.

Certain such liquid compositions of the invention may further comprise one or more preservatives and/or one or more stabilizers. Preservatives that are suitable for use in the compositions of the invention include, but are not limited to, edetic acid and their alkali salts such as disodium EDTA (also referred to as "disodium edetate" or "the disodium salt of edetic acid") and calcium EDTA (also referred to as "calcium edetate"), benzyl alcohol, methylparaben, propylparaben, butylparaben, chlorobutanol, phenylethyl alcohol, benzalkonium chloride, thimerosal, propylene glycol, sorbic acid, and benzoic acid derivatives. The preservatives should be used at a concentration of from about 0.001% to about 0.5% (w/v) in the final composition. The combination of benzalkonium chloride, used at a concentration of from about 0.001% to about 0.5% or preferably from about 0.005% to about 0.1% (w/v), and edetic acid (as a disodium salt), used at a concentration of from about 0.005% to about 0.1% (w/v), are suitable preservative/stabilizer combination used in the compositions of the present invention.

Certain compositions of the invention may further comprise one or more solubility-enhancing agents that are used to improve the solubility of the pharmaceutical compositions of the invention or of the active ingredients contained therein. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, and poly (ethylene glycols) (molecular weights of 200 to 600).

Certain compositions of the invention may further comprise one or more agents that are used to render the composition isotonic, particularly in those compositions in which water is used as a solvent. Such agents are particularly useful in compositions formulated for nasal or ocular application, since they adjust the osmotic pressure of the formulations to the same osmotic pressure as nasal or ocular secretions. Agents that are suitable for such a use in the compositions of the invention include, but are not limited to, sodium chloride, sorbitol, propylene glycol, dextrose, sucrose, and glycerine, and other isotonicity agents that are known in the art (see, e.g., Reich et al., "Chapter 18: Tonicity, Osmoticity, Osmolality and Osmolarity," in: *Remington: The Science and Practice of Pharmacy*, 20$^{th}$ Edition, Lippincott Williams and Wilkins, Philadelphia, Pa. (2000)).

It is frequently desirable that the compositions of the present invention that are to be administered in liquid form (including orally applied formulations) have a pH of about 4.5 to about 7.4, and preferably have a pH of about 5.5 to 7.1, for physiological reasons. Accordingly, in additional embodiments, the compositions of the invention may further comprise one or more buffering agents or combinations thereof, that are used to adjust and/or maintain the compositions into the desired pH range. Adjustment of pH or buffering agents that are suitable for use in the compositions of the invention include, but are not limited to, citric acid, sodium citrate, sodium phosphate (dibasic, heptahydrate form), and boric acid or equivalent conventional buffers, or combinations thereof. The appropriate amounts of buffers and buffering agents, or combinations thereof, that are to be used in the compositions of the invention are readily determined by those of ordinary skill without undue experimentation, particularly in view of the guidance contained herein and in standard formularies such as the United States Pharmacopoeia, *Remington: The Science and Practice of Pharmacy*, and the like, the disclosures of which are incorporated herein by reference in their entireties.

In certain embodiments, the liquid formulations of the invention, particularly those that are to be administered orally further comprise one or more taste-masking agents, one or more flavoring agents, and/or one or more sweetening agents, or a combination of such agents. Non-limiting examples of such substances include sucralose (about 0.001 to about 1%), sucrose (about 0.5 to about 10%), saccharin (including the salt forms: sodium, calcium, etc.) (about 0.01 to about 2%), fructose (about 0.5 to about 10%), dextrose (about 0.5 to about 10%), corn syrup (about 0.5 to about 10%), aspartame (about 0.01 to about 2%), acesulfame-K (about 0.01 to about 2%), xylitol (about 0.1 to about 10%), sorbitol (about 0.1 to about 10%), erythritol (about 0.1 to about 10%), ammonium glycyrrhizinate (about 0.01 to about 4%), thaumatin (Talin™) (about 0.01 to about 2%), neotame (about 0.01 to about 2%) mannitol (about 0.5 to about 5%), menthol (about 0.01 to about 0.5%), eucalyptus oil (about 0.01 to about 0.5%), camphor (about 0.01 to about 0.5%), natural and/or artificial flavors such as Artificial Custard Cream Flavor #36184 from International Flavors and Fragrances, Inc. (New York, N.Y.) (about 0.01 to about 1.0%), and the like. Sucralose, an intense sweetener marketed for food and beverage use as SPLENDA® by McNeil Nutritionals LLP (Fort Washington, Pa.), is especially effective as a sweetening and taste-masking agent in the compositions of the present invention, particularly when used at concentrations of from about 0.001% to about 1%, preferably at concentrations of from about 0.01% to about 0.5%, and more preferably at concentrations of from about 0.02% to about 0.2%, and most preferably from about 0.03% to about 0.15% (e.g., about 0.05%, about 0.06%, about 0.07%, about 0.08%, about 0.09%, about 0.10%, about 0.11%, about 0.12%, about 0.13%, about 0.14%, or about 0.15%), of the total composition. Sucralose has been shown to be useful as a taste modifying agent in oral delivery of certain pharmaceutical compositions, for example in sore throat spray products (see U.S. Pat. No. 6,319,513), oral suspensions (see U.S. Pat. Nos. 5,658,919 and 5,621,005), solid dosage forms (see U.S. Pat. No. 6,149,941), quick melt dosage forms (see U.S. Pat. No. 6,165,512) and mucosal delivery (see U.S. Pat. No. 6,552,024). Additional such compositions of the invention may comprise one or more additional taste-masking or flavoring agents, for example menthol at a concentration of from about 0.01% to about 1%, preferably at a concentration of from about 0.05% to about 0.1%.

In certain embodiments of the invention described herein, one or more of the active pharmaceutical ingredients contained in the present compositions are present in an immediate-release form. In additional embodiments of the invention, one or more of the active pharmaceutical ingredients contained in the present compositions, and suitably the metformin or pharmaceutically acceptable salt or ester thereof (e.g., metformin HCl), is present in such formulations in a sustained-release or extended-release form. As a practical matter, the phrases "immediate-release," "sustained-release" and "extended-release" are terms of art, the definitions of which will be readily familiar to those of ordinary skill in the relevant arts in view of knowledge that is readily available and well-known in those arts, particularly in medicine, pharmaceutical formulations and pharmacology. Suitable such embodiments will optimally comprise a therapeutically effective amount or dose of one or more of the active pharmaceutical ingredients, suitably metformin or a pharmaceutically acceptable salt or ester thereof, and one or more pharmaceutically acceptable carriers or excipients that provide a sustained or extended release of the one or more active pharmaceutical ingredients over a period of time after administration to the patient. In certain such embodiments, the one or more active pharmaceutical ingredients, suitably metformin or a pharmaceutically acceptable salt or ester thereof, is: 1) coated with one or more sustained release components; 2) bound to a cation exchanger; 3) reacted with one or more osmotically active substances and coated with a semi-permeable membrane and a hole is bored into the membrane; or 4) embedded in, or is bound to, one or more substances selected from of the group consisting of digestible fats, indigestible fats, polymers and swelling agents. In certain such embodiments, the metformin of the present invention will be either in an inner core coated with a layer containing the statin, the inhibitor of the renin-angiotensin system, and the antiplatelet agent, or in a second layer apart from the layer containing the statin, the inhibitor of the renin-angiotensin system, and the antiplatelet agent.

Methods for preparing sustained release tablets, capsules, caplets, pellets and the like, as well as excipients for use in the sustained release formulations of the present invention, are well known in the art, and can be found, for example, throughout the detailed description section and the Examples of U.S. Pat. No. 5,271,946, the disclosure of which is incorporated herein by reference in its entirety for all purposes.

As discussed in U.S. Pat. No. 5,271,946, the sustained release formulations of the present invention can be obtained as follows:

1. Through binding of one or more of the active ingredients contained in the present compositions, suitable metformin or a pharmaceutically acceptable salt or ester thereof (e.g., metformin HCl), and optionally one or more additional active agents such as those described herein, to physiologically acceptable cation exchangers. The following may, for example, be used as such cation exchangers: acrylic and methacrylic resins with exchangeable protons, acid groups: COO— e.g. Amberlite™ IRP-64 Polystyrene resins with exchangeable Na⁺, acid groups: $SO_3$—, e.g. Amberlite™ IRP-69.

2. Coating of active ingredient particles, granulate or pellet grains or active ingredient-containing tablets with coatings of the following substances, or mixtures of the following substances: hydroxypropylmethyl cellulose phthalate- or acetate succinate; cellulose-, starch-, as well as polyvinyl acetate phthalate; carboxymethyl cellulose; hypromellose; carbopol starch acetate; cellulose acetate; polyvinyl acetate; methylcellulose phthalate, methylcellulose succinate, methyl cellulose phthalate succinate as well as methyl cellulose phthalic acid half ester; zein; ethyl cellulose as well as ethyl cellulose succinate; shellac; gluten; ethylcarboxyethyl cellulose; ethacrylate-maleic acid anhydride copolymer; maleic acid anhydride vinyl methyl ether copolymer; sterol maleic acid copolymerizate; 2-ethylhexylacrylate maleic acid anhydride; crotonic acid vinyl acetate copolymer; glutaminic acid/ glutaminic acid ester copolymer; carboxymethylethyl cellulose glycerin mono-octanoate; cellulose acetate succinate; polyarginin; fats, oils, waxes, fatty alcohols; anionic polymerizates of methacrylic acid and methacrylic acid esters (Eudragit™L, Eudragit™S); copolymerizates of acrylic and methacrylic acid esters with a low ammonium group (Eudragit™RS) content, as well as copolymers of acrylic and methacrylic acid esters and trimethyl ammonium methacrylate (Eudragit™RL), copolymerizates of acrylic acid ethyl- and methacrylic acid methyl esters 70:30 (Eudragit™NE 30 D), copolymerizates of acrylic acid, methacrylic acid as well as their esters (ratio of the free carboxyl groups to the ester groups for example 1:1) (Eudragit™L 30 D).

Such sustained release formulations may also contain conventional softeners (e.g. dibutyl sebacate, citric and tartaric acid esters, glycerin and glycerin esters, phthalic acid esters and similar substances). It also is possible to add water-soluble substances such as polyethylene glycols, polyvinylpyrrolidone, copolymerizates of polyvinylpyrrolidone and polyvinyl acetate, hydroxypropyl cellulose, hydroxypropylmethyl cellulose. The addition of solids such as talcum and/or magnesium stearate to the coating is also possible.

Organic acids (such as for example citric acid, tartaric acid, maleic, fumaric ascorbic acid) may also be incorporated into the pellet grains, granulate grains or tablets.

3. Coating of pressed disks, tablets, granulates containing the active ingredient(s), suitably metformin or salt/ester thereof, and optionally one or more additional active agents such as those described herein, and one or more osmotically active substances, (e.g. mannitol, sorbitol and the like) with a semi-permeable membrane, e.g. of 70 to 90 weight % of cellulose acetate and hydroxypropylmethyl cellulose or hypromellose (30 to 10 weight %).

Other osmotically active substances that can be used include organic and inorganic compounds or soluble substances which generate an osmotic pressure gradient as compared to the outer liquid via the semi-permeable wall. Osmotically active agents or osmotically active compounds include magnesium sulfate, magnesium chloride, sodium chloride, lithium chloride, potassium sulfate, potassium hydrogen phosphate, urea, saccharose and the like. Other osmotically active agents are disclosed in U.S. Pat. Nos. 3,854,770, 4,077,407 and 4,235,236, the disclosures of each of which are incorporated herein by reference in their entireties.

Semi-permeable materials which can be used as polymers for osmosis and reverse osmosis are, for example: cellulose acylate, cellulose diacylate, cellulose triacylate, cellulose acetate, cellulose diacetate, cellulose triacetate, β-glucan acetate, acetaldehyde dimethyl acetate, cellulose acetate ethyl carbamate, polyamide, polyurethane, sulphonated polystyrene, cellulose acetate phthalate, cellulose acetate methyl carbamate, cellulose acetate succinate, cellulose acetate dimethylamino acetate, cellulose acetate chloracetate, cellulose dipalmitate, cellulose dioctanoate, cellulose dicaprylate, cellulose dipentanate, cellulose acetate valerate, cellulose acetate-p-toluene sulphonate, cellulose acetate butyrate, ethyl cellulose, selectively permeable polymers which are formed by joint precipitation of a polycation and a polyanion as disclosed in U.S. Pat. Nos. 3,173,876, 3,276,586, 3,541,005, 3,541,006 and 3,546,142, the disclosures of which are incorporated by reference herein in their entireties. Coatings of this type in semi-permeable membranes may for example also be effected according to U.S. Pat. Nos. 4,455,143 and 4,449,983, the disclosures of which are incorporated by reference herein.

The proportion of osmotically active substance can be from about 10 to about 800 parts by weight, suitably about 20 to about 600, and more suitably about 50 to about 400 parts by weight, based on 1 part by weight of active ingredient that is to be sustainably or extendedly released. The amount of coating substances applied is such that the semi-permeable membrane is about 50 to about 500 µm, suitably about 100 to about 300 µm thick.

4. Embedding of or binding of one or more active ingredients in the present compositions, suitably metformin (or salt/ester thereof), and/or any other optional additional active agent(s) to the following substances or mixtures of these substances:

Digestible fats, such as triglycerides of saturated fatty acids, $C_8H_{16}O_2$ to $C_{18}H_{36}O_2$, and mixtures thereof, peanut oil and hydrated peanut oil, castor oil and hydrated castor oil, olive oil, sesame oil, cottonseed oil and hydrogenated cottonseed oil, corn oil, wheat germ oil, sunflower seed oil, cod liver oil, mixtures of mono-, di- and triesters of palmitic and stearic acid with glycerine, glycerine trioleate, diglycol stearate, stearic acid.

Indigestible fats or fat-like substances, for example esters of aliphatic saturated or unsaturated fatty acids (2 to 22 carbon atoms, in particular 10 to 18 carbon atoms) with monovalent aliphatic alcohols (1 to 20 carbon atoms), carnauba wax, beeswax, fatty alcohols (straight chain or branched) of chain length $C_8H_{17}OH$ to $C_{30}H_{61}OH$, in particular $C_{12}H_{25}OH$ to $C_{24}H_{49}OH$.

Polymers such as polyvinyl alcohol, polyvinyl chloride, polyacrylic acid (Carbopol™); anionic polymerizates of methacrylic acid and methacrylic acid esters (Eudragit™L, Eudragit™S), acrylic and methacrylic acid ester copolymerizates with trimethyl ammonium methacrylate (Eudragit™RL, Eudragit™RS).

Copolymerizates of ethyl acrylates and methyl methacrylates (Eudragit™NE 30 D), as well as of acrylic acid, methacrylic acid as well as esters thereof (ratio of free carboxyl groups to ester groups 1:1) (Eudragit™L 30 D), polyethylene, polyglycolic acid, polyhydroxybutyric acid, polylactic acid, copolymers of lactic acid and glycolic acid (manufacturer: Boehringer Ingelheim), copolymers of lactic acid and ethylene oxide, copolymers of glycolic acid and ethylene oxide, copolymers of lactic acid and hydroxybutyric acid, hydroxypropylmethyl cellulose-phthalate or -acetate succinate; cellulose acetate phthalate, starch acetate phthalate as well as polyvinyl acetate phthalate; carboxymethyl cellulose; methylcellulose phthalate, -succinate, -phthalate succinate, methyl cellulose phthalic acid half ester; zein; ethyl cellulose; shellac, gluten; ethylcarboxyethyl cellulose; ethacrylate maleic acid anhydride copolymer; maleic acid anhydride vinyl methyl ether copolymer; styrene maleic acid copolymerizate; 2-ethylhexyl acrylate maleic acid anhydride; crotonic acid vinyl acetate copolymer; glutaminic acid/glutaminic acid ester copolymer; carboxymethyl cellulose glycerine mono-octanoate; cellulose acetate succinate; polyarginine; cross-linked alginate; cross-linked gelatin.

Swelling agents such as methyl cellulose, hydroxypropyl cellulose, hydroxypropyl methyl cellulose (Pharmacoat, Methocel E (propylene glycol ether of methyl cellulose)), alginic acid and their salts (Na—, Ca— salt, also mixtures of sodium alginate and calcium salts such as $CaHPO_4$), starch, carboxymethyl starch, carboxymethyl cellulose and their salts (e.g. Na— salts), galacto mannan, gum arabic, karaya rubber, ghatti gum, agar-agar, carrageen, xanthan rubber, guar rubber and its derivatives, carob bean flour, propylene glycol alginate, pectin, tragacanth.

The amounts of active ingredient(s), suitably metformin or salt/ester thereof, and optionally one or more additional active agents such as those described herein, in the formulations of the invention are the same as those described elsewhere herein for non-sustained-release (i.e., "immediate release" or "delayed release") dosage forms of the compositions of the invention.

Suitable exemplary sustained release components are:

(a) Cation exchangers: Sodium poly(styrene, divinylbenzene)sulphonate (e.g. Amberlite™IRP 69). Suitably 3 to 10 parts of Amberlite™IRP 69 are for example used per 1 part of active pharmaceutical ingredient.

(b) Coating substances: Hydroxypropylmethyl cellulose phthalate, suitably at 1.5 to 3 parts of hydroxypropyl methyl cellulose phthalate 55 are used per 1 part of active ingredient, e.g., one or more insulin sensitizers, one or more sulfonylureas and/or one or more biguanides. Ethyl cellulose, suitably 0.1 to 1 part of ethyl cellulose are used per 1 part of active ingredient. Eudragit resins, for example Eudragit™RS 0.01 to 0.1 part of Eudragit™RS per 1 part of active pharmaceutical ingredient.

(c) Semi-permeable layers with osmotically acting active substance containing core and outlet openings: Coating with 100 to 300 μm thick layer of 82% cellulose acetate and 18% hydroxypropyl methyl cellulose.

(d) Embedding substances: Hydrocolloids e.g. hydroxypropyl methyl cellulose: 2 to 10 parts of hydrocolloid per 1 part of active ingredient. Eudragit™RS: 10 to 15 parts of Eudragit™RS per 1 part of active ingredient. Glycerineditripalmito stearate (e.g. Precirol Ato 5) 1 to 10 parts of Precirol Ato 5 per 1 part of active pharmaceutical ingredient.

The requisite release of one or more of the active pharmaceutical ingredients included in the present formulations (e.g., one or more insulin sensitizers, one or more sulfonylureas and one or more biguanides, e.g., metformin, suitably metformin HCl, and optionally any additional active agents) of 0.5 to 200 mg per hour suitably occurs within the desired range through the parameters described herein. Should it be desired to achieve a specific release rate within this range it is possible, for example, to proceed as follows:

1. The preparation of the coating or embedding of the active substance in the described manner.

2. Testing of the release of active substance from the dosage form using 0.1 N HCl (2 hours) and phosphate buffer pH 6.8 (subsequently) as release medium.

3. (a) Should too much substance be released: Increase of the proportion of the sustained release component and/or reduction of the proportion of water-soluble auxiliary substances. Reduction of the proportion of osmotically active substance.

(b) Should too little substance be released: Reduction of the proportion of the sustained release component and/or increase of the proportion of water soluble auxiliary substances. Increase of the proportion of osmotically active substance.

In one embodiment, a release rate of about 20 mg to about 200 mg of metformin HCl per hour can be achieved, allowing the use of metformin HCl at doses as low as 500 mg/day but up to about 5000 mg/day if desired.

Excipients for use with the pharmaceutical compositions of the invention, generally are selected from among excipients which have good moisture qualities in the sense that the substance will not adversely affect the active agent fine particle dose (FPD) for the shelf life of the product regardless of normal changes in ambient conditions during storage. Suitable "dry" excipients are well known in the art and include those disclosed herein. For example, lactose can be selected as a dry excipient, or lactose monohydrate can be used in a formulation with a pharmaceutical composition of the invention (and optionally one or more additional active agents, such as those described herein). Lactose has the inherent property of having a low and constant water sorption isotherm. Excipients having a similar or lower sorption isotherm can also be used.

As discussed throughout, and in a further aspect of the present invention, one or more pharmaceutical compositions of the invention may be mixed or formulated with one or more additional active agents such as those described herein in the dry powder or other formulations. The present invention thus also encompasses the use of one or more pharmaceutical compositions of the invention, e.g., wherein a combination of one or more pharmaceutical compositions of the invention with one or more other agents, such as those described herein, constitutes a formulation from which metered doses are then produced, filled and sealed into dry, moisture-tight, high barrier seal containers intended for insertion into a DPI to be administered according to a particular dosing regime or as needed by the user.

A sealed, dry, high barrier container can be loaded with a powder form of a pharmaceutical composition of the invention in the form of a blister and may comprise a flat dose bed or a formed cavity in aluminum foil or a molded cavity in a polymer material, using a high barrier seal foil against ingress of moisture, e.g. of aluminum or a combination of aluminum and polymer materials. The sealed, dry, high barrier container may form a part of an inhaler device or it may form a part of a separate item intended for insertion into an inhaler device for administration of pre-metered doses.

Methods of Use

In additional embodiments of the invention, the invention provides methods of treating mammals afflicted with certain diseases, particularly with cardiovascular disease and other related disorders described elsewhere herein and that will be familiar to the ordinarily skilled artisan, using the compositions of the present invention. In related embodiments, the invention provides such methods of treatment or prevention by administering to said mammal a cardiovascular disease-treating or cardiovascular disease-preventing amount of a composition comprising ramipril, atorvastatin, an antiplatelet agent such as acetylsalicylic acid, and lycopene.

In related embodiments, the invention provides methods of reducing or preventing the progression of cardiovascular disease to a more advanced stage of CVD in a patient, comprising administering to a patient suffering from CVD, a therapeutically effective amount of one or more of the compositions of the present invention. Certain such methods of the invention comprise administering to the patient one or more compositions of the invention that are described herein, and one or more additional active agents.

According to certain such methods of the invention, one or more compositions of the present invention are administered to a patient, such as a patient suffering from or predisposed to cardiovascular disease, via any suitable mode of administration as described elsewhere herein.

In particular such methods, the compositions are administered to the mammal via oral administration. Methods of oral administration can be accomplished via liquid or solid form, and particularly in solid form such as in tablet or capsule form, using approaches and mechanisms described elsewhere herein and others that will be familiar to the ordinarily skilled artisan.

Suitable dosages (e.g., amounts, volumes, etc.) of the compositions of the invention will be apparent from the description herein, including the Examples below. Thus in one embodiment, the invention provides a pharmaceutical composition for the treatment of cardiovascular diseases, including the underlying causes, but not limited to hypercholesterolemia and hypertension, in a mammal. Exemplary pharmaceutical compositions for use in methods according to this aspect of the invention comprise one or more cholesterol lowering agents, one or more angiotensin converting enzyme inhibitors, and one or more antiplatelet agents. In certain such embodiments, the methods of the invention, the pharmaceutical composition for the treatment of cardiovascular disease in a mammal comprises ramipril, atorvastatin, at least one antiplatelet agent such acetylsalicylic acid, and lycopene. Suitable amounts of each active ingredient present in the compositions that are advantageously used in this aspect of the invention will be apparent from the description herein, and from the Examples herein.

In particular such methods, the compositions of the invention are administered to the patient in a single dosage comprising a therapeutically effective amount of each of one or more cholesterol lowering agents, one or more angiotensin converting enzyme inhibitors, and one or more antiplatelet agents, and optionally one or more additional active ingredients. Suitable compositions for use in exemplary such methods of the invention include those compositions described herein comprising atorvastatin, ramipril, acetylsalicylic acid, and metformin each in a therapeutically effective (i.e., Metabolic Syndrome-treating or Metabolic Syndrome-preventing amount).

In particular such methods, the compositions of the invention are administered to the patient in a single, daily dosage form, once per day. In alternative such methods, the compositions are administered to the patient two or more (i.e., two, three, four or more) times per day, or as needed according to the particular treatment regiment designed by the patient's physician.

The amount of the compositions of the invention administered each time throughout the treatment period can be the same; alternatively, the amount administered each time during the treatment period can vary (e.g., the amount administered at a given time can be more or less than the amount administered previously). For example, doses given during maintenance therapy may be lower than those administered during the acute phase of treatment. Appropriate dosing schedules depending on the specific circumstances will be apparent to persons of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Stability and Compatibility Testing of Microtablets

The compatibility between each active ingredient (metformin, atorvastatin, ramipril, and acetylsalicylic acid) and different excipient(s) was tested. Each active ingredient and excipient(s) were mixed together. The particle size distribution and flow properties of the blended active ingredient and excipient(s) was assessed. Following mixing, the resulting powder was used for preparation of a microtablet. Microtablets were formed using direct compression, dry granulation, wet granulation and/or combinations or modifications thereof. The microtablets of each active ingredient had a diameter of about 3 mm or less. Additional microtablets were prepared that had a diameter of less than 2.5 mm. The stability and release characteristics of each active ingredient microtablet were assessed. Each active ingredient microtablet has different properties from the other active ingredient microtablets. Excipient(s) that were found to be compatible with each active ingredient were utilized in the microtablet preparation described in Example 2.

Example 2

Polypill Capsule Formulation Comprising Metformin, Atorvastatin, Ramipril and Acetylsalicylic Acid A polypill capsule containing 500 mg of metformin, 20 mg of atorvastatin, 5 mg of ramipril, and 81 mg of acetylsalicylic acid, was prepared as follows (Table 1).

TABLE 1

Exemplary capsule formulation comprising metformin, atorvastatin, ramipril, and acetylsalicylic acid.

| Active Ingredient | Amount per polypill capsule (mg) range | mg per polypill capsule, exemplary formulation |
|---|---|---|
| Metformin | 100-10000 | 500 |
| Atorvastatin | 5-140 | 20 |
| Ramipril | 1-80 | 5 |
| Acetylsalicylic acid | 20-500 | 81 |

Methods

Mix Process

Metformin was passed through a mesh screen and collected in a clean polyethylene container. Metformin was then mixed with the excipient(s) that resulted in maximum stability and desired release characteristics of the metformin microtablet, as identified in Example 1.

Atorvastatin was passed through a mesh screen and collected in a clean polyethylene container. Atorvastatin was then mixed with the excipient(s) that resulted in maximum stability and desired release characteristics of the atorvastatin microtablet, as identified in Example 1.

Ramipril was passed through a mesh screen and collected in a clean polyethylene container. Ramipril was then mixed with the excipient(s) that resulted in maximum stability and desired release characteristics of the ramipril microtablet, as identified in Example 1.

Acetylsalicylic acid was passed through a mesh screen and collected in a clean polyethylene container. Acetylsalicylic acid was then mixed with the excipient(s that resulted in maximum stability and desired release characteristics of the acetylsalicylic acid microtablet, as identified in Example 1.

Tableting

Following mixing, the resulting powder of each active ingredient/excipient blend was individually compressed in a tablet press machine to form an active ingredient microtablet with a diameter of less than 2.5 mm.

Polypill Capsule Formation

Equivalent amounts of metformin, atorvastatin, ramipril and acetylsalicylic acid microtablets were mixed together and encapsulated in suitable size hard gelatin capsules to yield the final product.

Example 3

Polypill Capsule Formulation Comprising Metformin, Atorvastatin, Ramipril and Acetylsalicylic Acid A polypill capsule containing 850 mg of metformin, 20 mg of atorvastatin, 5 mg of ramipril, and 81 mg of acetylsalicylic acid, was prepared as follows (Table 2).

TABLE 2

Exemplary capsule formulation comprising metformin, atorvastatin, ramipril, and acetylsalicylic acid.

| Active Ingredient | mg per polypill capsule |
| --- | --- |
| Metformin | 850 |
| Atorvastatin | 20 |
| Ramipril | 5 |
| Acetylsalicylic acid | 81 |

Polypill capsules were prepared as described in Example 2.

Example 4

Evaluation of Metformin, Atorvastatin, Ramipril and Acetylsalicylic Acid in the Treatment of Metabolic Syndrome A 40-year old woman who presented with chest discomfort that was subsequently diagnosed to have Metabolic Syndrome. Physical examination showed an obese woman with a body weight of 82 Kg, height 162 cm, with BMI of 32 Kg/m$^2$. Blood pressure (BP) was 160/110 mmHg, fasting blood sugar (FBS) was 150 mg/dL, triglyceride (Tg) 215 mg/dL, total cholesterol (TC) 320 mg/dL, LDL-C 212 mg/dL, HDL-C 37 mg/dL, and HbA1c of 8.46%. She was Heated with a polypill capsule described in Example 3, containing metformin 850 mg, atorvastatin 20 mg, ramipril 5 mg and acetylsalicylic acid 81 mg, once a day over the next 6 months. She was regularly followed in order to evaluate adherence to therapy, regular follow-up and potential side effects. After this intervention period fasting biochemical results showed FBS 115 mg/dL, HbA1c 6.69%, TC 235 mg/dL, LDL-C 123.7 mg/dL, HDL-C 40 mg/dL, Tg 119 mg/dL and her weight was reduced to 74 kg. 11-dehydro thromboxane B2 level and platelet aggregation were reduced respectively by 75% and 90% with respect to the baseline. Adherence to therapy was 100%. With this intervention the patient had a considerable modification of the risk factors of Metabolic Syndrome.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for the treatment or prevention of Metabolic Syndrome in a patient comprising administering to said patient in need of such treatment or prevention once a day in a single dose of a pharmaceutical composition comprising about 20 mg atorvastatin, about 5 mg ramipril, about 850 mg metformin, and about 81 mg acetylsalicylic acid.

2. The method of claim 1, wherein the metformin is present in sustained-release or extended release form.

3. The method of claim 1, wherein the pharmaceutical composition is administered as a tablet, capsule, syrup or solution.

4. The method of claim 1, wherein the atorvastatin, the ramipril, the metformin and the acetylsalicylic acid are each in the form of a microtablet.

5. The method of claim 4, wherein the microtablets of atorvastatin, ramipril, metformin and acetylsalicylic acid are intermixed and encapsulated within a hard gelatin capsule.

6. The method of claim 1, wherein the pharmaceutical composition is contained in a kit together with a label containing instructions to administer the pharmaceutical composition once per day to a patient in need thereof.

* * * * *